United States Patent [19]
Lax et al.

[11] Patent Number: 5,672,153
[45] Date of Patent: Sep. 30, 1997

[54] MEDICAL PROBE DEVICE AND METHOD

[75] Inventors: Ronald G. Lax, Grassvalley; James A. Baker, Palo Alto, both of Calif.

[73] Assignee: Vidamed, Inc., Menlo Park, Calif.

[21] Appl. No.: 311,814

[22] Filed: Sep. 26, 1994

Related U.S. Application Data

[63] Continuation-in-part of Ser. No. 929,638, Aug. 12, 1992, abandoned, and Ser. No. 12,370, Feb. 2, 1993, Pat. No. 5,370,675.

[51] Int. Cl.$^6$ ................................................. A61B 17/39
[52] U.S. Cl. ................................................. 604/22
[58] Field of Search .................... 604/19–22, 53, 604/164, 280; 606/39, 32, 45, 96, 113, 115, 116, 138, 156, 101, 102

[56] References Cited

U.S. PATENT DOCUMENTS

| | | |
|---|---|---|
| Re. 32,066 | 1/1986 | Leveen . |
| 1,879,249 | 9/1932 | Hansaker ........................... 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. . |
| 3,595,239 | 7/1971 | Petersen . |
| 3,598,108 | 8/1971 | Jamshidi . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,941,121 | 3/1976 | Olinger et al. . |
| 3,942,530 | 3/1976 | Northeved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,121,592 | 10/1978 | Whalley . |
| 4,136,566 | 1/1979 | Christensen . |
| 4,137,920 | 2/1979 | Bonnet . |
| 4,154,246 | 5/1979 | Leveen . |

(List continued on next page.)

FOREIGN PATENT DOCUMENTS

| 10858/92 | 8/1992 | Australia . |
|---|---|---|
| 0219216 A1 | 4/1987 | European Pat. Off. . |

(List continued on next page.)

OTHER PUBLICATIONS

U.I. Dept. of Health and Human Services, MMWR 41: 401–404 vol. 41, No. 23, (Jun. 12, 1992).

Transuretheral µwave Thermotherapy for Prostatism: Early Mayo Foundation Experience: Blute, Mayo Clinic Proceedings: vol. 67 May 92 pp. 417–421.

(List continued on next page.)

*Primary Examiner*—Manuel Mendez
*Attorney, Agent, or Firm*—Flehr, Hohbach, Test, Albritton & Herbert

[57] ABSTRACT

A method and device for medical treatment of a tissue mass. The method comprises introducing a catheter along a body duct to a zone adjacent to the target tissue to be treated. A flexible stylet comprising a radiofrequency electrode partially enclosed within a non-conductive sleeve is moved from the catheter through a catheter port in the side wall of the catheter and through surrounding tissue into a target tissue to be treated. An outward force is exerted on the wall of the body duct by means of an inflatable balloon attached to the catheter and heat is generated in the target tissue by passing electrode current from the exposed area of the electrode into the target tissue.

59 Claims, 13 Drawing Sheets

U.S. PATENT DOCUMENTS

| | | |
|---|---|---|
| 4,204,549 | 5/1980 | Paglione . |
| 4,224,929 | 9/1980 | Furihata . |
| 4,228,809 | 10/1980 | Paglione ............................. 128/804 |
| 4,237,898 | 12/1980 | Whalley . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. . |
| 4,312,364 | 1/1982 | Convert et al. . |
| 4,336,809 | 6/1982 | Clark . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman . |
| 4,448,198 | 5/1984 | Turner . |
| 4,452,236 | 6/1984 | Utsugi . |
| 4,470,407 | 9/1984 | Hussein ................................ 606/2 |
| 4,494,539 | 1/1985 | Zenitani et al. . |
| 4,552,554 | 11/1985 | Gould et al. . |
| 4,562,838 | 1/1986 | Walker . |
| 4,565,200 | 1/1986 | Cosman . |
| 4,568,329 | 2/1986 | Mahurkar . |
| 4,580,551 | 4/1986 | Siegmund et al. . |
| 4,594,074 | 6/1986 | Anderson et al. . |
| 4,601,296 | 7/1986 | Yerushalmi . |
| 4,612,940 | 9/1986 | Kasevich et al. . |
| 4,658,836 | 4/1987 | Turner . |
| 4,660,560 | 4/1987 | Klein . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer . |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,781,186 | 11/1988 | Simpson et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger . |
| 4,905,667 | 3/1990 | Foerster et al. . |
| 4,906,230 | 3/1990 | Maloney et al. . |
| 4,907,589 | 3/1990 | Cosman . |
| 4,911,148 | 3/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,940,064 | 7/1990 | Desai . |
| 4,943,290 | 7/1990 | Rexroth ................................. 606/49 |
| 4,946,449 | 8/1990 | Davis, Jr. . |
| 4,949,706 | 8/1990 | Thon . |
| 4,950,267 | 8/1990 | Ishihara et al. . |
| 4,955,877 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,982,724 | 1/1991 | Saito et al. . |
| 4,994,062 | 2/1991 | Nishigaki et al. . |
| 4,998,932 | 3/1991 | Rosen et al. . |
| 4,998,933 | 3/1991 | Eggers et al. . |
| 5,002,558 | 3/1991 | Klein et al. . |
| 5,003,991 | 4/1991 | Takayama et al. . |
| 5,007,437 | 4/1991 | Sterzer . |
| 5,007,908 | 4/1991 | Rydell . |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,045,056 | 9/1991 | Behl . |
| 5,045,072 | 9/1991 | Castillo . |
| 5,055,109 | 10/1991 | Gould et al. . |
| 5,057,105 | 10/1991 | Malone et al. . |
| 5,057,106 | 10/1991 | Kasevich et al. . |
| 5,057,107 | 10/1991 | Parins . |
| 5,059,851 | 10/1991 | Corl et al. . |
| 5,060,660 | 10/1991 | Gambale et al. . |
| 5,071,418 | 12/1991 | Rosenbaum ............................. 606/45 |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox ................................ 606/42 |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,195,968 | 3/1993 | Lundquist et al. . |
| 5,197,963 | 3/1993 | Parins ................................. 606/41 |
| 5,201,732 | 4/1993 | Parins et al. . |
| 5,207,672 | 5/1993 | Roth . |
| 5,220,927 | 6/1993 | Astrahan et al. . |
| 5,222,953 | 6/1993 | Dowlatshahi . |
| 5,228,441 | 7/1993 | Lundquist . |
| 5,234,004 | 8/1993 | Hascoet et al. ....................... 607/102 |
| 5,235,964 | 8/1993 | Abenaim . |
| 5,249,585 | 10/1993 | Turner et al. ........................ 607/99 |
| 5,254,088 | 10/1993 | Lundquist et al. . |
| 5,257,451 | 11/1993 | Edwards et al. . |
| 5,273,524 | 12/1993 | Fox et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |

| | | |
|---|---|---|
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,312,392 | 5/1994 | Hofstetter et al. . |
| 5,313,943 | 5/1994 | Houser et al. . |

FOREIGN PATENT DOCUMENTS

| | | |
|---|---|---|
| 0370890 | 5/1990 | European Pat. Off. . |
| 0453071 | 10/1991 | European Pat. Off. . |
| 0495443 | 7/1992 | European Pat. Off. . |
| 521264A2 | 1/1993 | European Pat. Off. . |
| 2848484 | 5/1979 | Germany . |
| 2941060A1 | 4/1980 | Germany . |
| 3218314 | 6/1983 | Germany . |
| 3247793A1 | 7/1983 | Germany . |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| WO92/10142 | 6/1992 | WIPO . |
| 9221278 | 12/1992 | WIPO . |
| 9221285 | 12/1992 | WIPO . |
| 9304727 | 4/1993 | WIPO . |
| 9308755 | 5/1993 | WIPO . |
| 9308756 | 5/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| 9320893 | 10/1993 | WIPO . |
| WO93/25136 | 12/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

OTHER PUBLICATIONS

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market . . . " Stephen Scala Nov. 19, 1991 pp. 1–32.

Diasonics, Brochure DIA 2000 171 CRF May 1988.

Perinchery, Narayan, "Neoplasms of the Prostate Gland," pp. 378–409 (Date Unknown).

Urology 5th ed., Storz, Jan. 1992.

Standard Urology Product Catalog, CIRCON ACMI: Stanford (1992).

Chang, Raymond J. et al, American Heart Journal, 125: 1276–1283 (May, 1993).

Cosman, Eric R. et al, Sterostatic and Functional Neurosurgery, pp. 2490–2499 (Date Unknown).

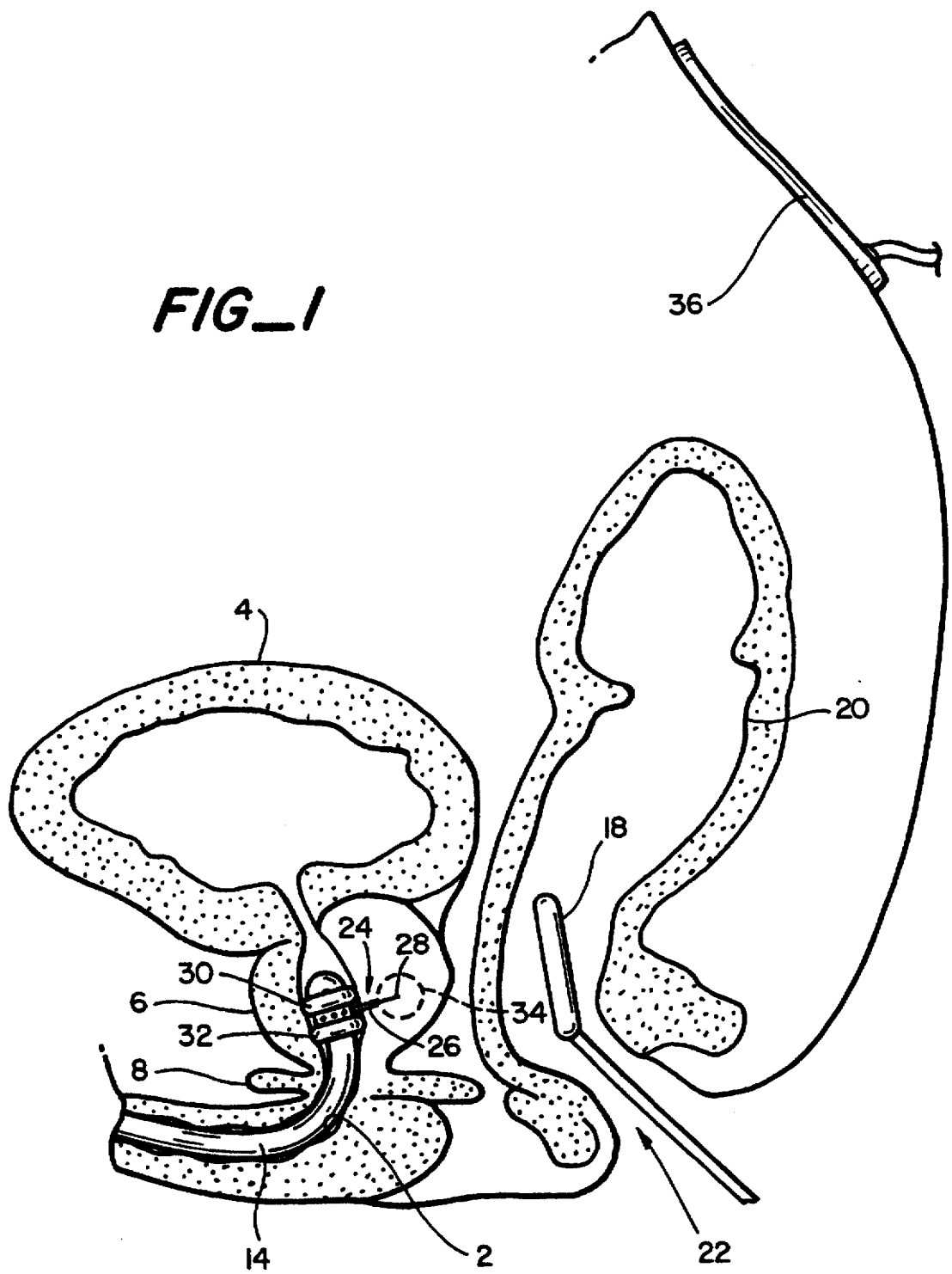
FIG_1

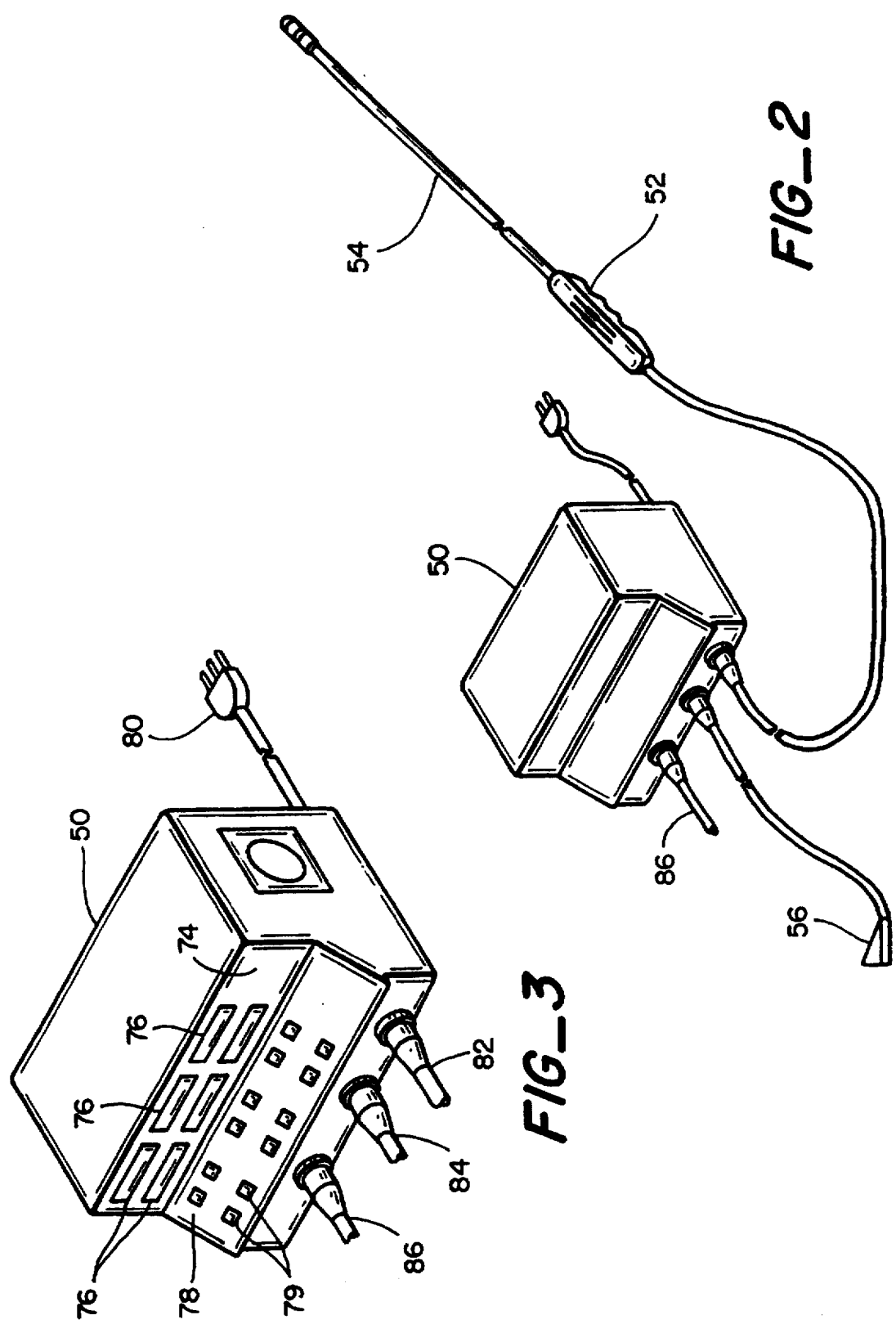

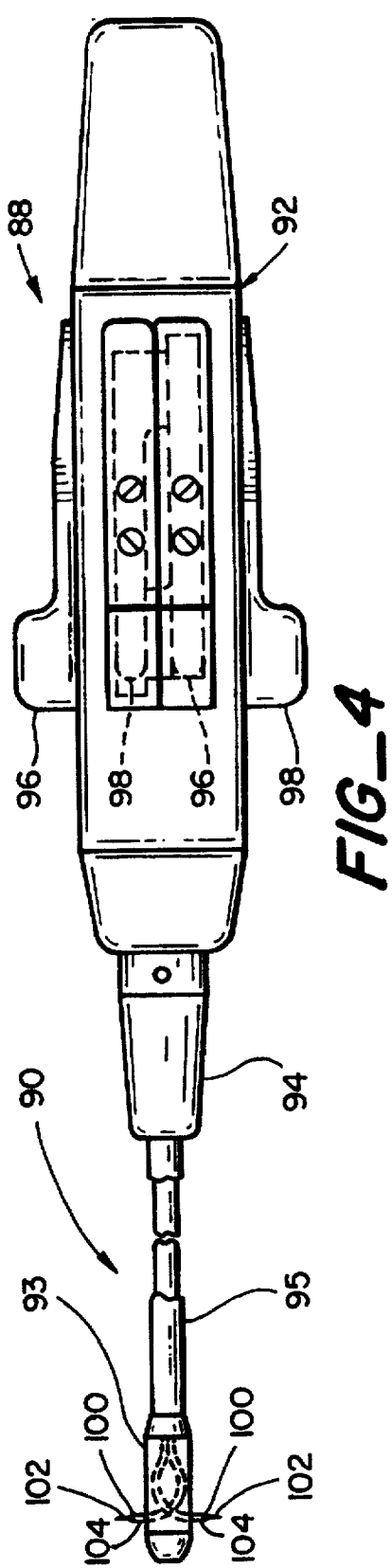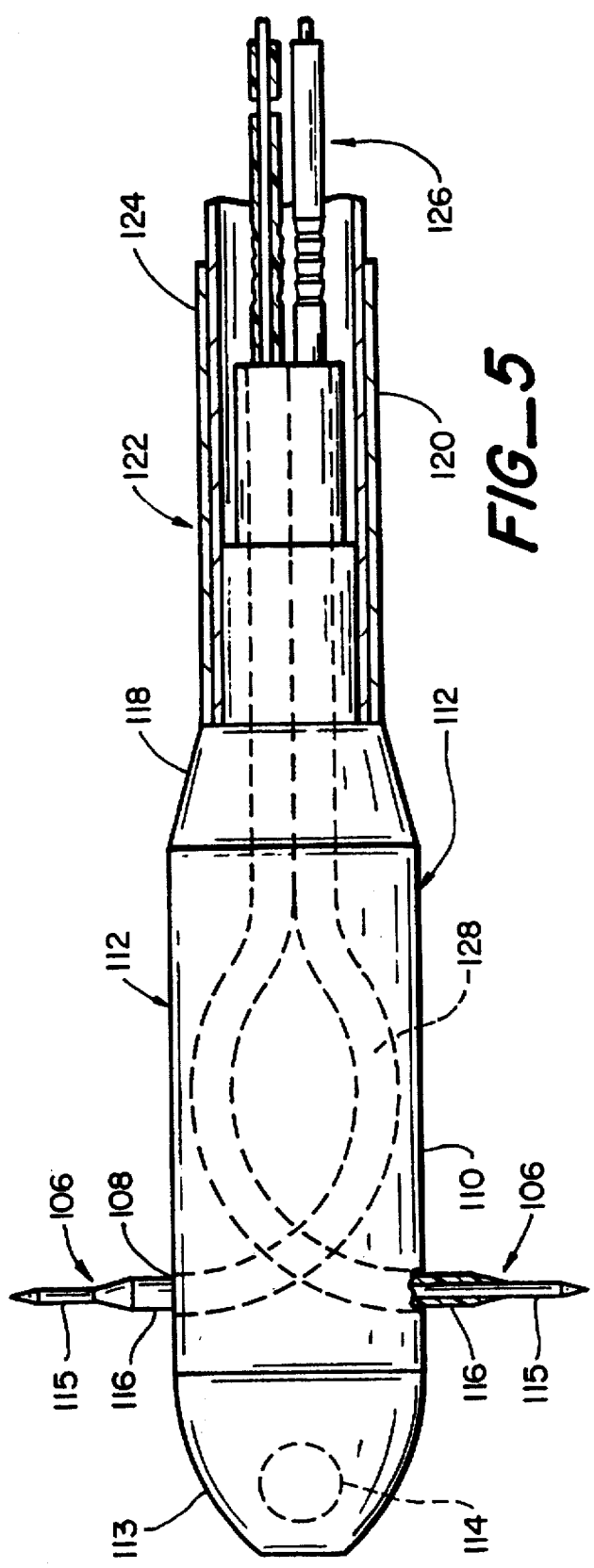

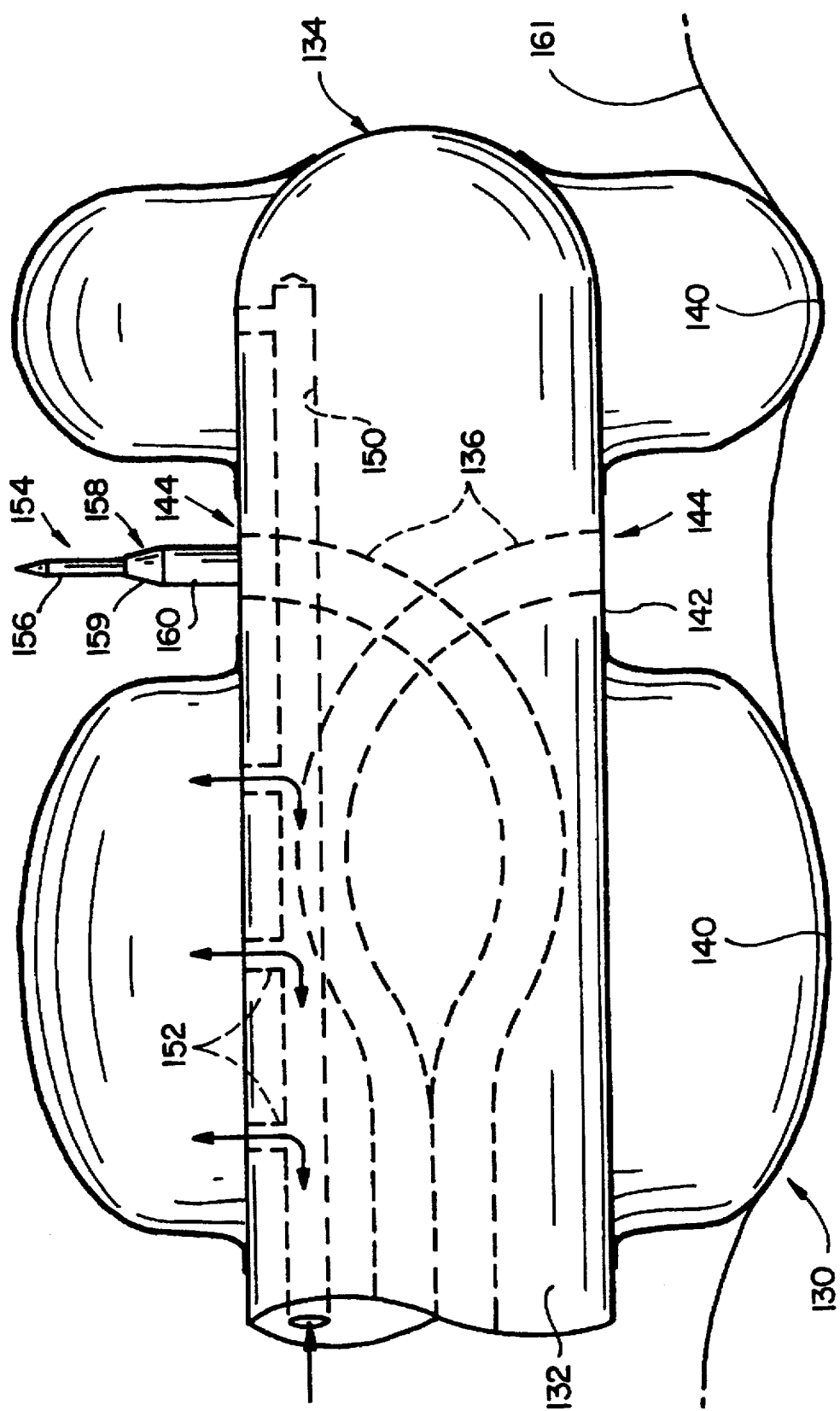
FIG_6

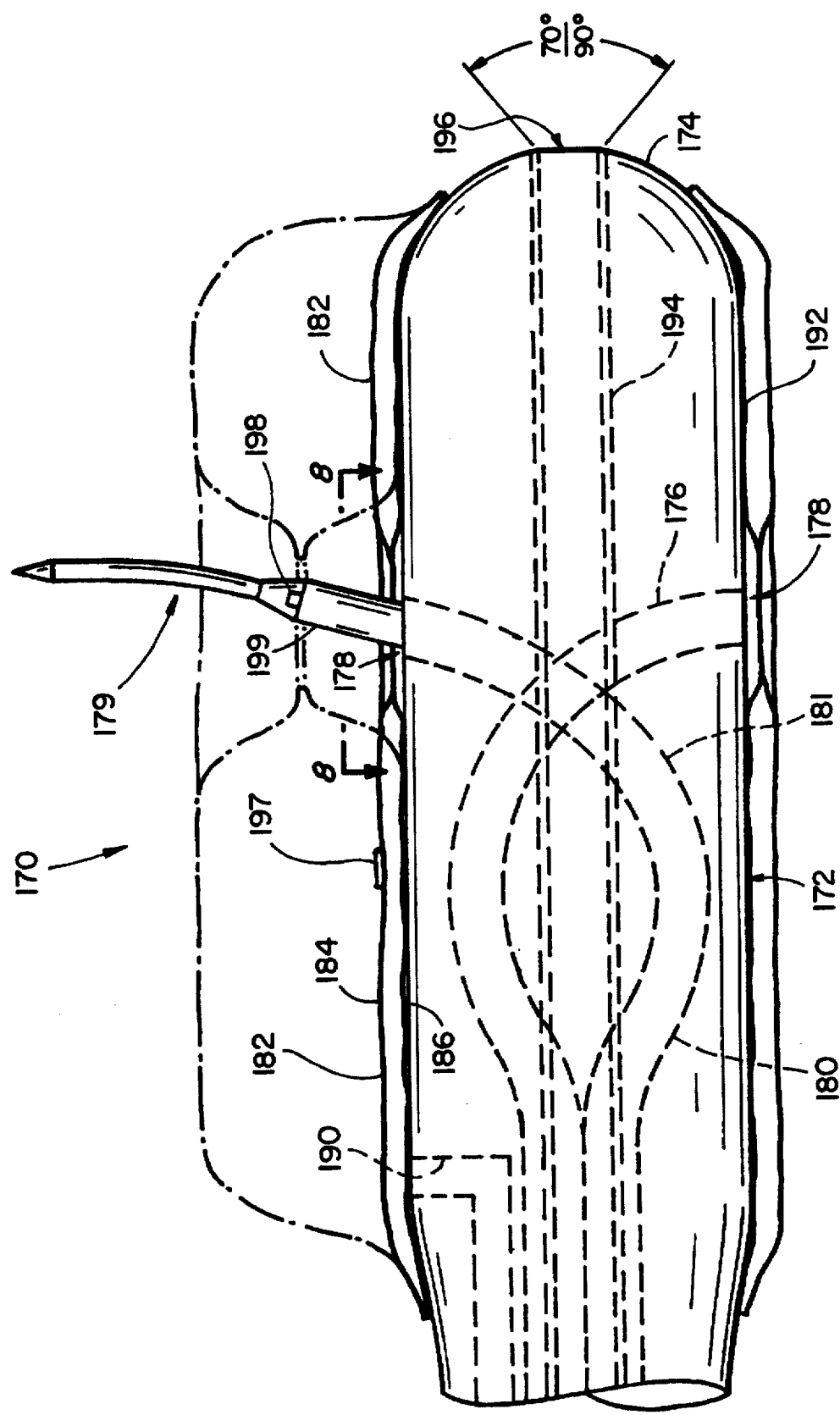
FIG_7

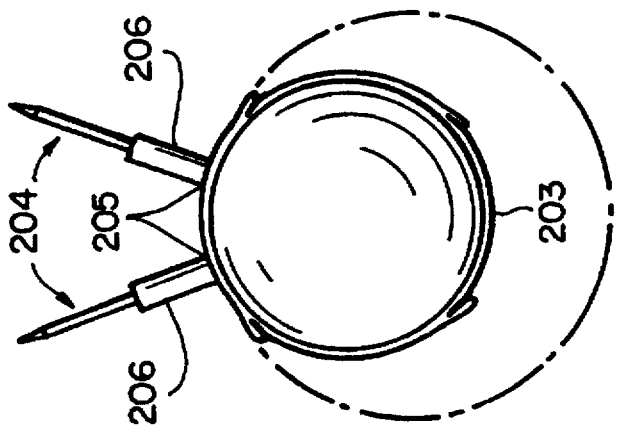
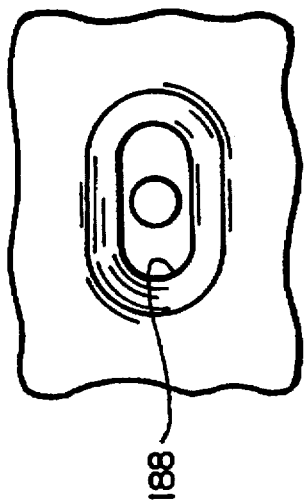
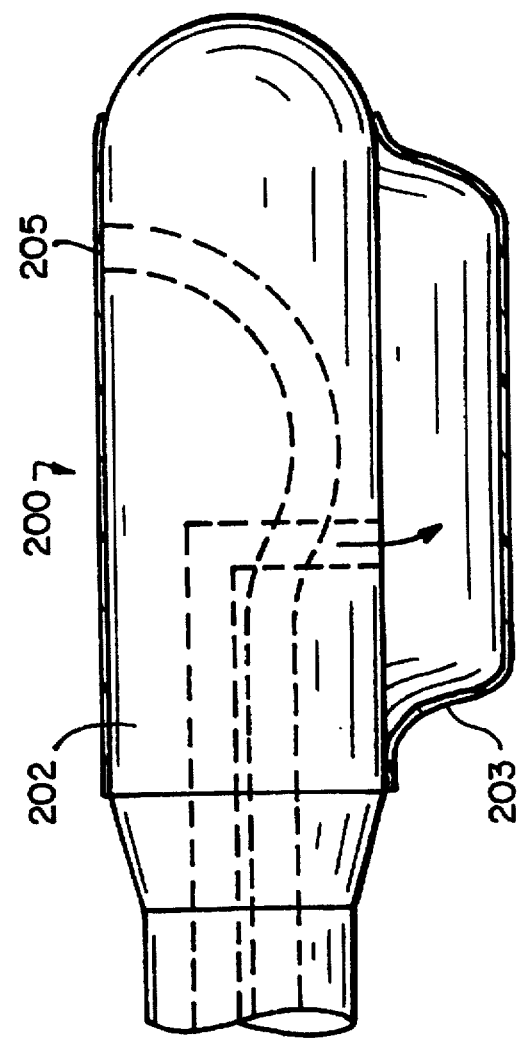

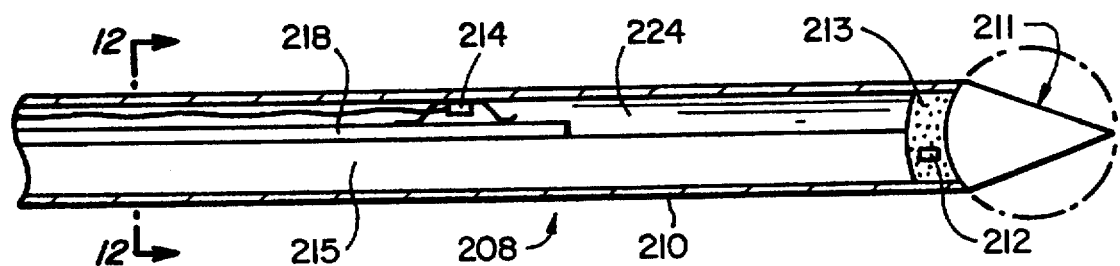
FIG_11
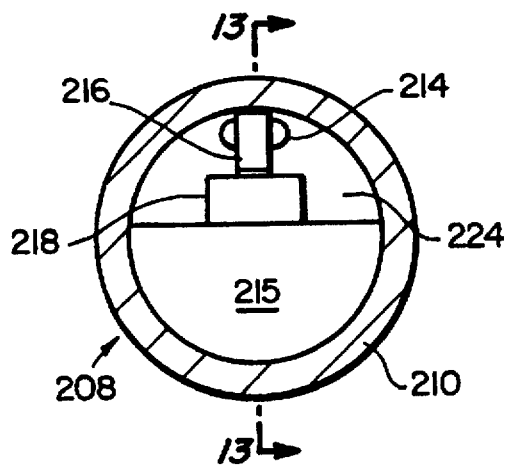
FIG_12
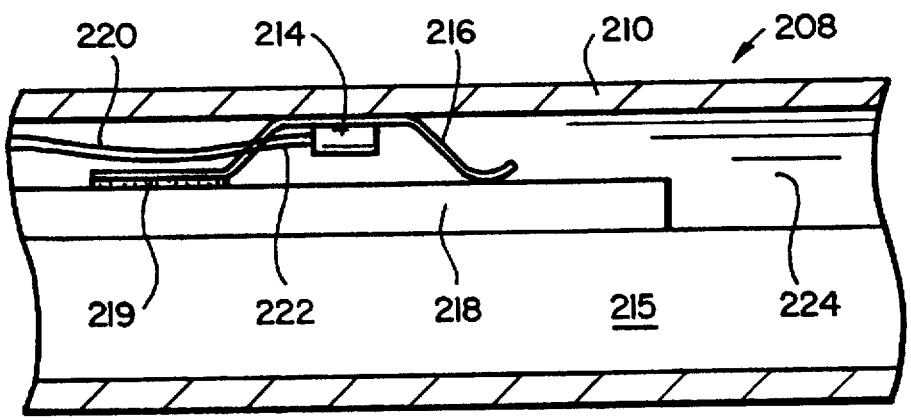
FIG_13

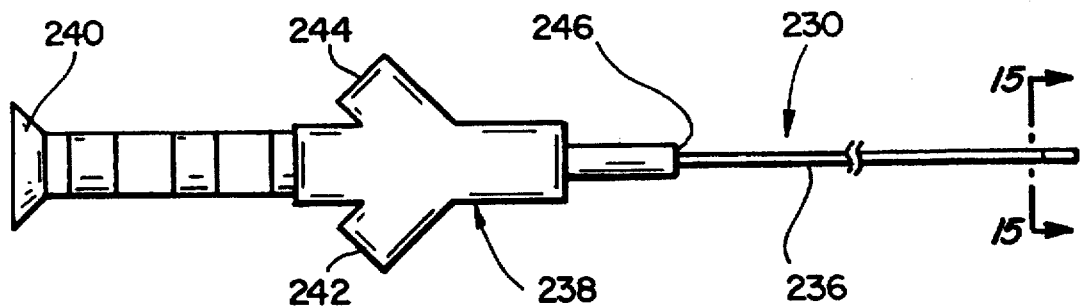
FIG_14
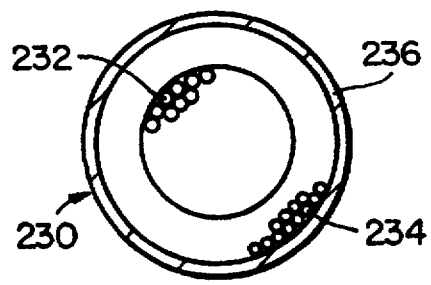
FIG_15
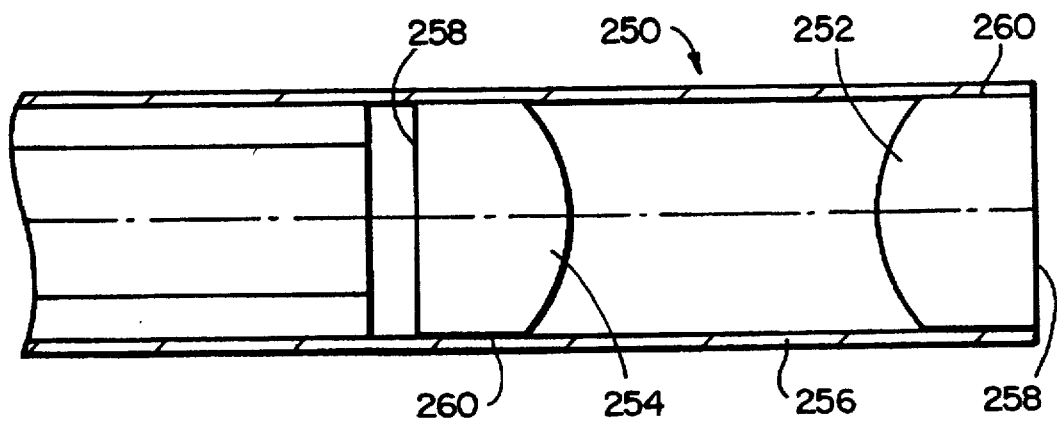
FIG_16

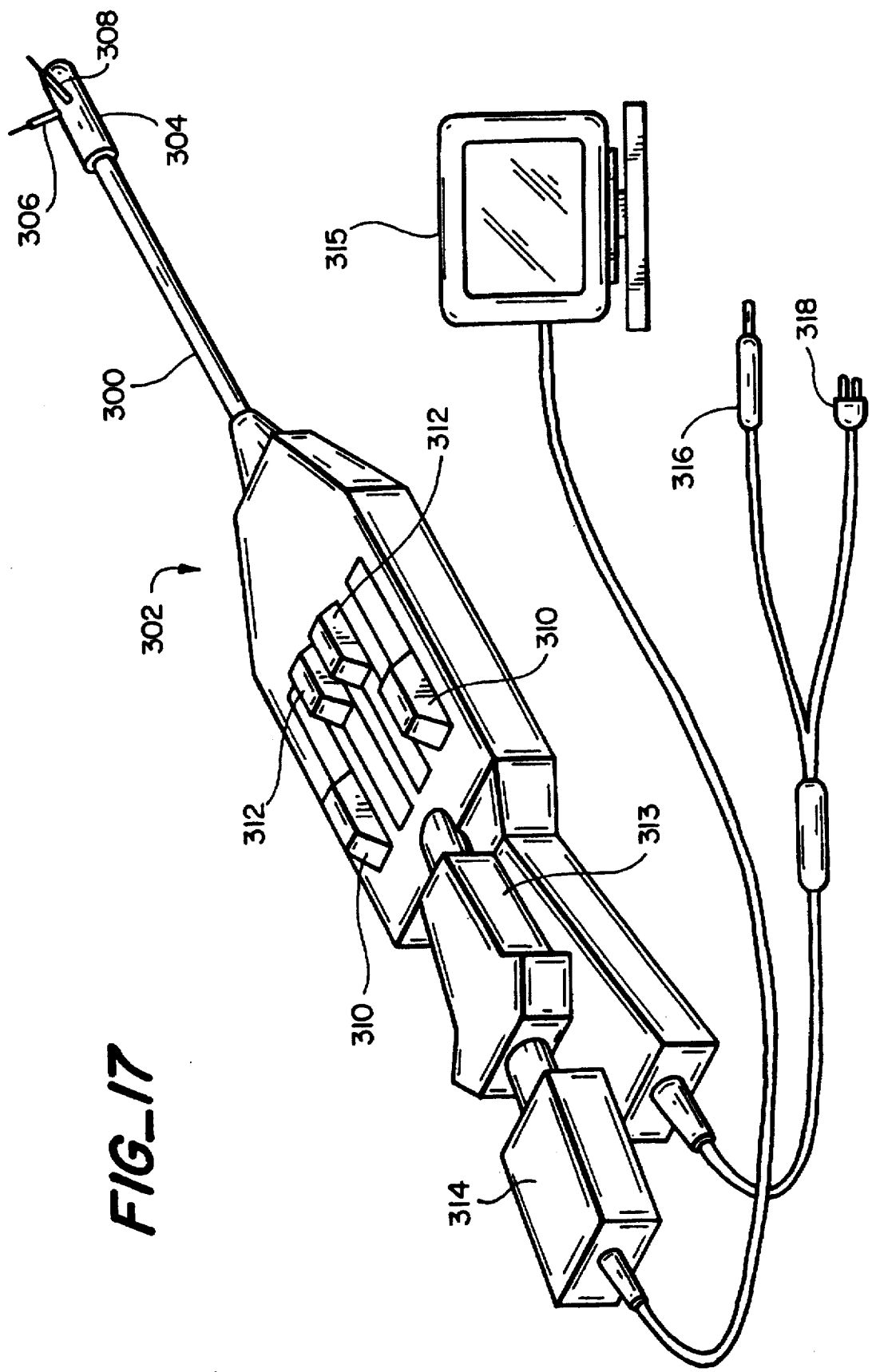
FIG_17

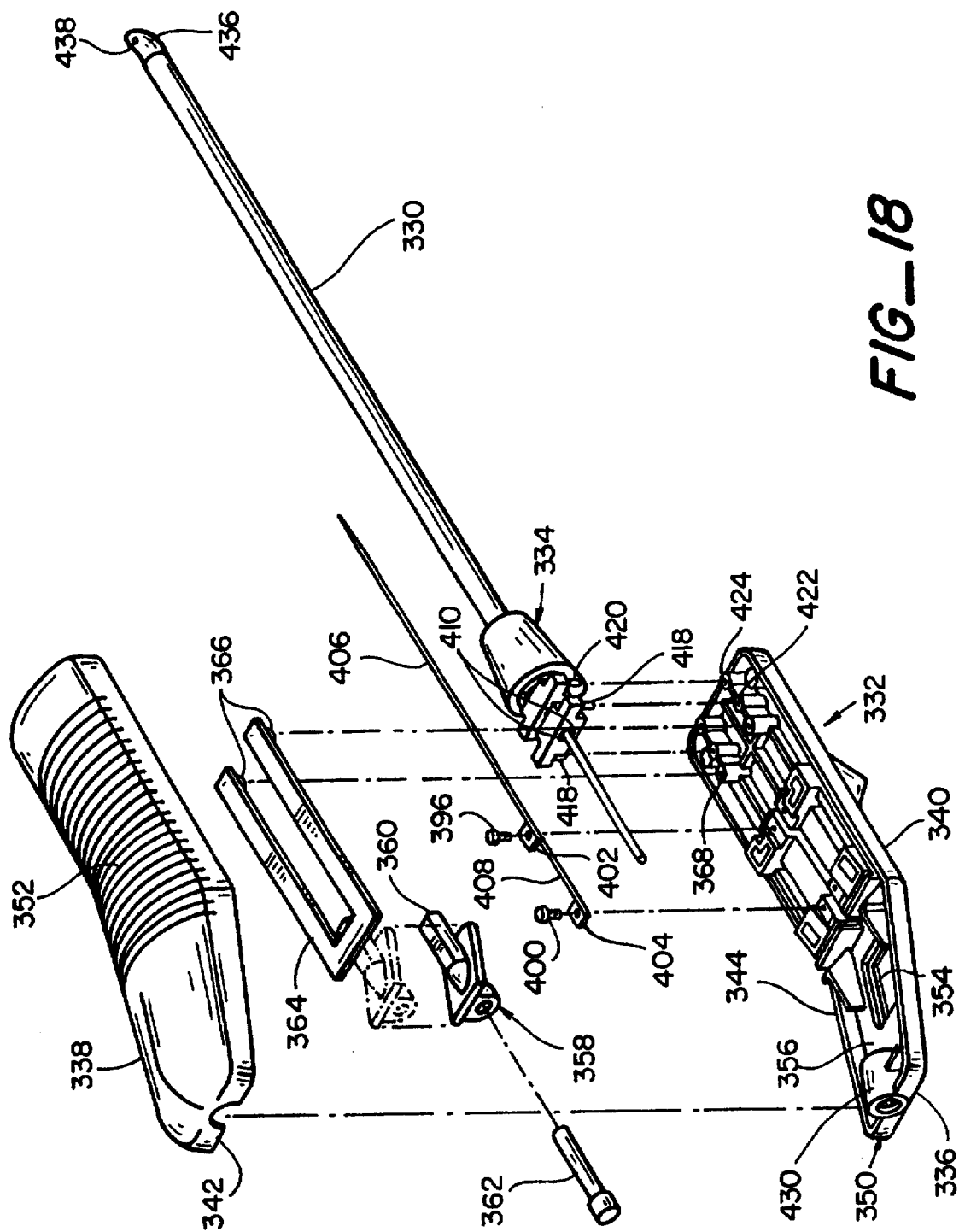

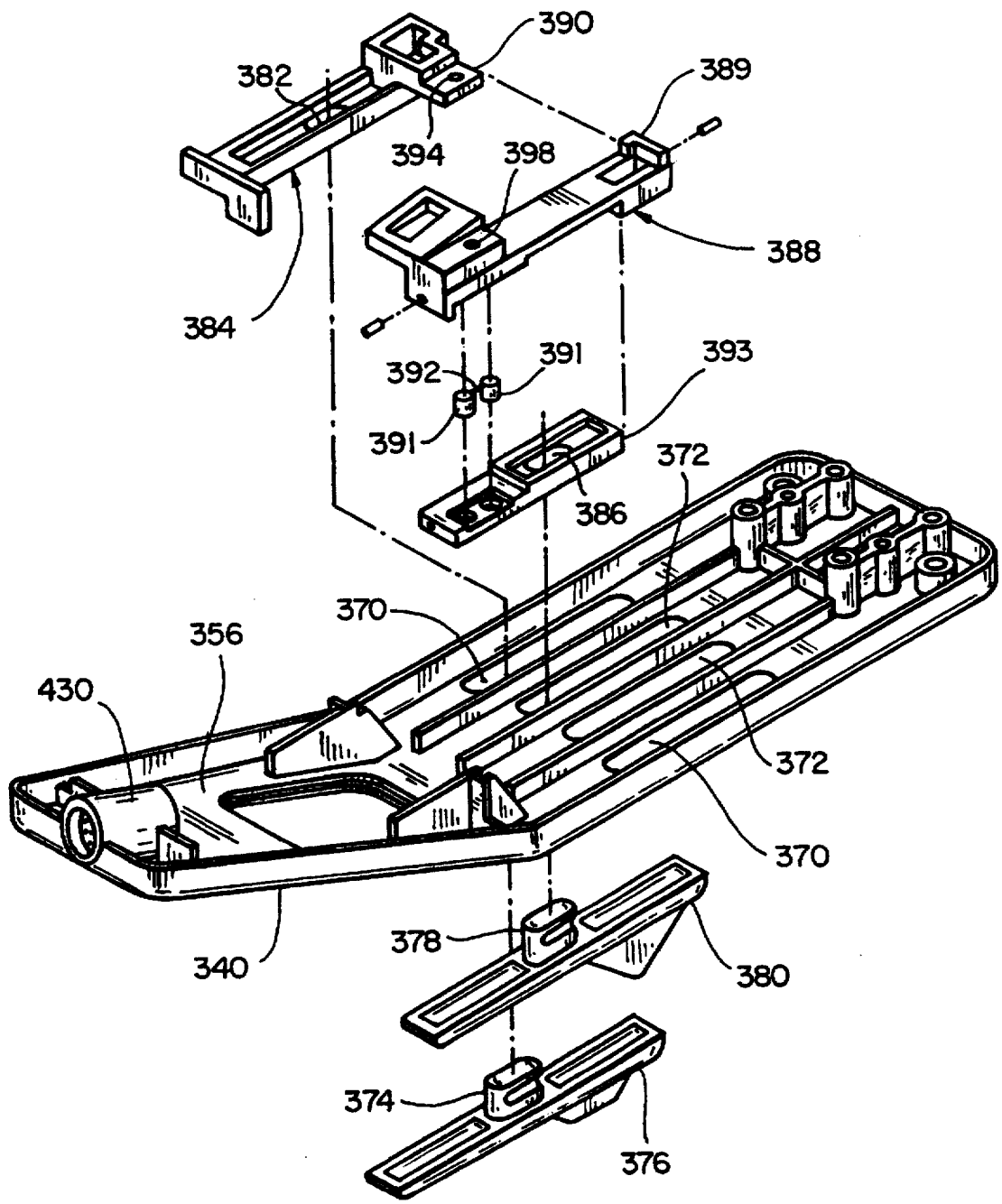
FIG_19

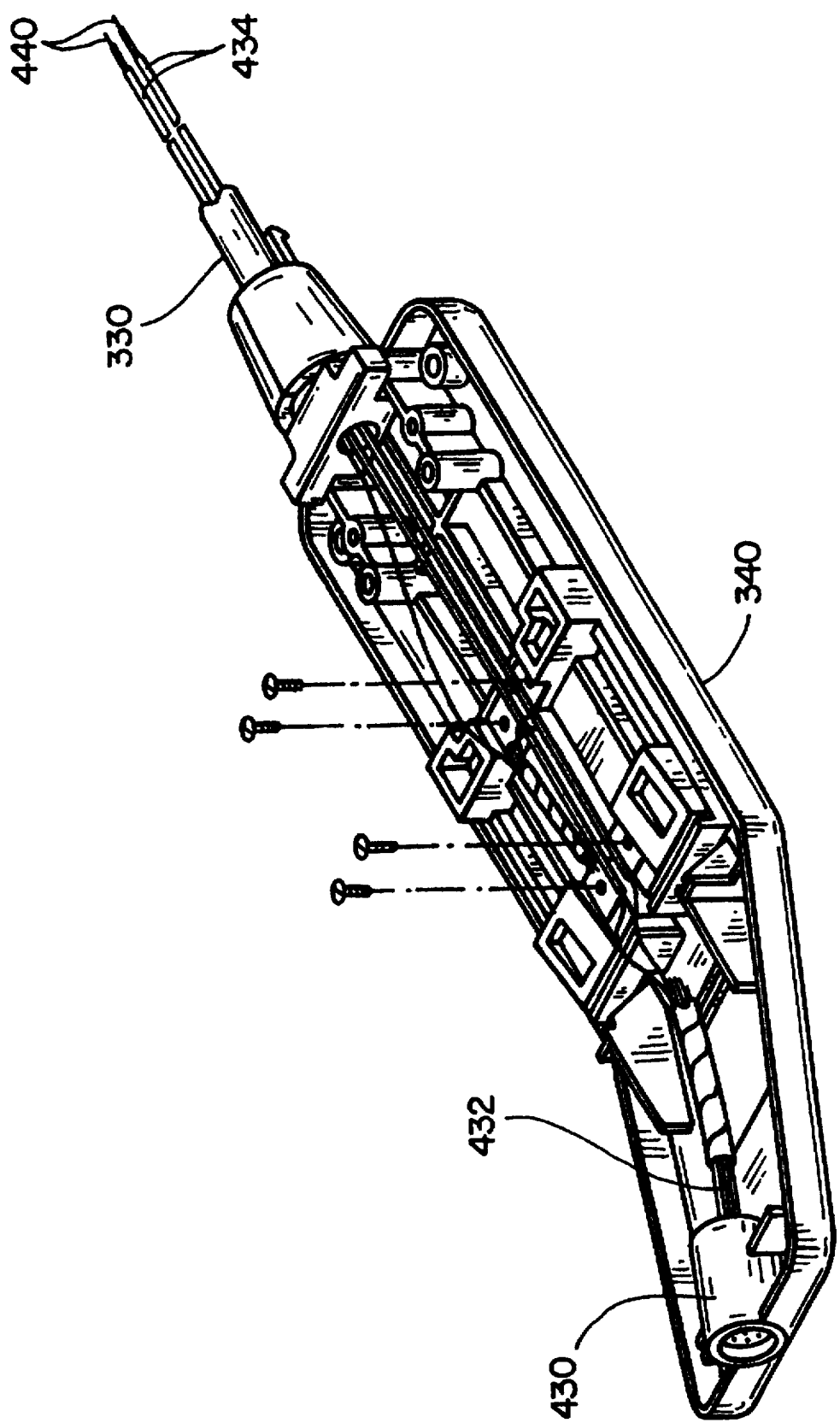
FIG_20

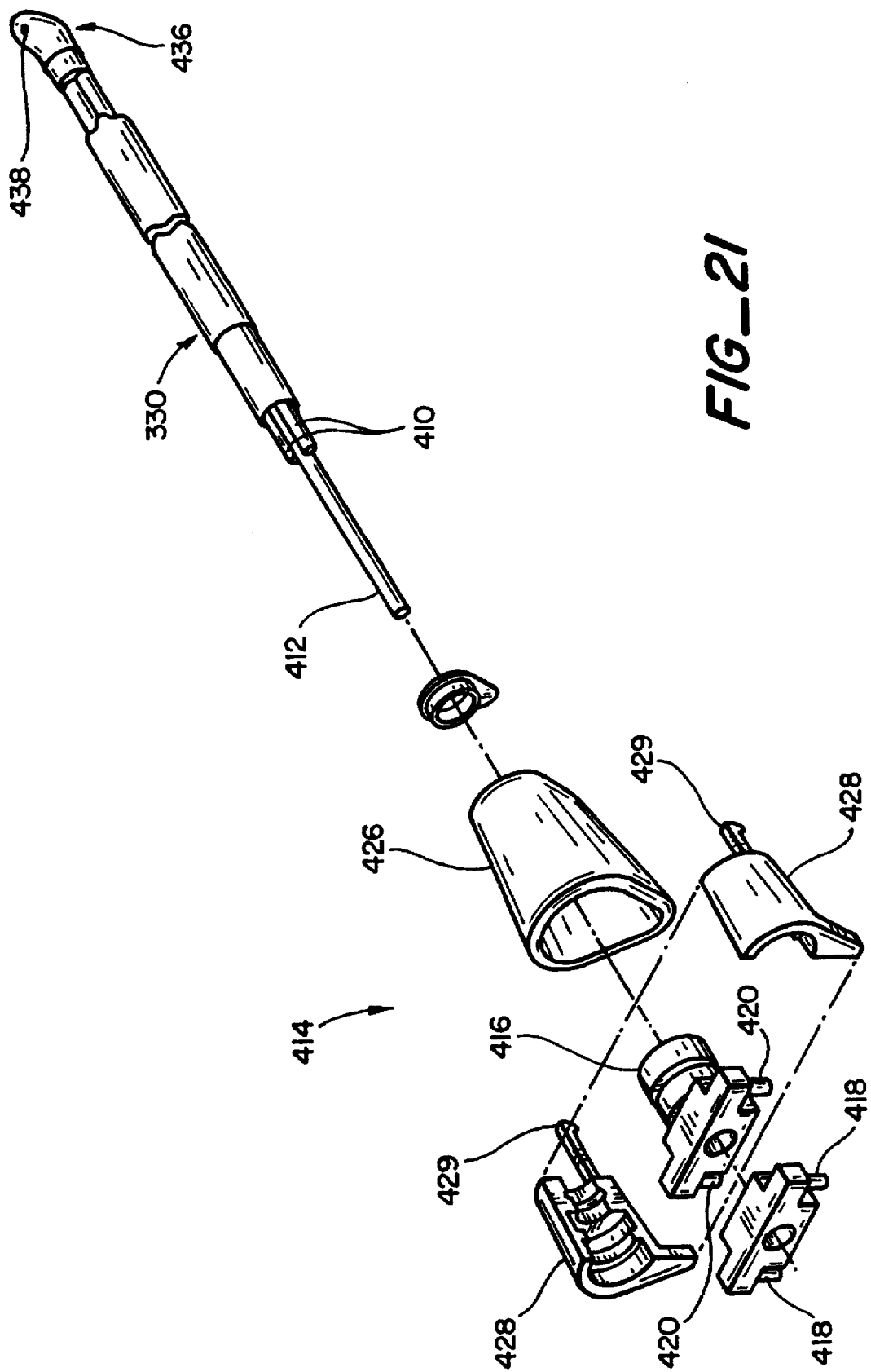

MEDICAL PROBE DEVICE AND METHOD

RELATIONSHIP TO COPENDING APPLICATION

This application is a continuation-in-part of application Ser. No. 07/929,638 filed Aug. 12, 1992, abandoned and application Ser. No. 08/012,370 filed Feb. 2, 1993 now U.S. Pat. No. 5,370,675.

FIELD OF THE INVENTION

This invention is directed to a unique device and method for penetrating body tissues for medical purposes such as tissue destruction and fluid substance delivery, for example. The device penetrates tissue to the precise target selected in order to deliver energy to the tissue and/or deliver substances. It limits this activity to the precise preselected site, thereby minimizing trauma to normal surrounding tissue and achieving a greater medical benefit. This device is a catheter-like device for positioning a treatment assembly in the area or organ selected for medical treatment with at least one stylet in the catheter, mounted for extension from a stylet port in the side wall of the catheter through surrounding tissue to the tissue targeted for medical activity.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by middle to older aged men. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and embarrassment. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 350,000 patients per year undergo surgery for removal of prostatic tissue in the United States.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and impotence. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as impotence are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operation site is not accessible with normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 khz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal modules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the modules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

OBJECTS AND SUMMARY OF THE INVENTION

It is the principal object of this invention to provide a device and method for penetrating tissue, through intervening tissue to the precise target tissue selected for a medical action such as tissue destruction. In particular it is an object of the invention is to provide a thermal destruction device having a dilatation balloon for expanding constricted passageways, and limiting the thermal activity to the precise preselected site, thereby minimizing the trauma and achieving a greater medical benefit.

Thus it is an object of this invention to provide a device and method for tissue destruction of body tissue which delivers the therapeutic energy directly into a target tissue while minimizing effects on its surrounding tissue.

Another object of this invention is to provide a thermal destruction device which gives the operator more information about the temperature and other conditions created in both the tissue targeted for treatment and the surrounding tissue. In particular it is an object of this invention to provide a thermal destruction device having a fiber optic scope to provide more control over the physical placement of the stylet and over the parameters of the tissue destruction process.

The medical probe device of this invention comprises a catheter having a control end and a probe end, the probe end including a stylet guide housing having a stylet port in a side thereof and stylet guide means defining a stylet path towards the stylet port for directing a flexible stylet outward through the stylet port and through intervening tissue to a target tissue. It has a stylet positioned in the stylet path, the stylet comprising a radiofrequency electrode partially enclosed within a non-conductive sleeve. The catheter further has an inflation fluid delivery lumen extending along the catheter to the stylet guide housing. The probe end includes an inflation balloon means in communication with the inflation fluid delivery lumen.

The inflation balloon can include at least one annular dilation balloon positioned adjacent the stylet port and expandable outwardly against surrounding tissue.

The catheter can define a fiber optic channel extending parallel to a longitudinal axis of the catheter and having a proximal opening for receiving a fiber optic scope, and a distal viewing port. The fiber optic scope can include viewing fibers, light fibers and a liquid supply connector for supplying a flushing liquid to the probe end of the catheter.

The non-conductive sleeve can be mounted for longitudinal movement on the electrode to expose a selected portion of the electrode in the target tissue.

The electrode can comprise a tube having an axial lumen extending longitudinally therethrough. The tube can be made of nickel-titanium. A temperature sensor can be movably disposed in the axial lumen for longitudinal movement therein. A temperature sensor can be mounted on the inflation balloon means and/or the distal end of the non-conductive sleeve for indicating the temperature in the tissue abutting the balloon means the tissue at the distal end of the sleeve, respectively.

The stylet guide housing can include at least two of said stylet ports and a corresponding number of stylets. The stylet guide housing can include two stylet ports positioned approximately in a plane perpendicular to the longitudinal axis of the housing. The catheter can be made from a polycarbonate.

An ultrasound imaging means can be located at the distal end of the catheter for providing a signal indicative of the position of the catheter in the body.

The stylet guide means can define a stylet path from an axial orientation in the catheter through a curved portion to a lateral orientation at the stylet port. The curved portion can be a radius which is sufficient to permit sliding deployment of the stylet in the stylet path. The stylet guide means can define a stylet path having a first curved portion curved away from the stylet port and a second curved portion, continuing from the first curved portion, which is curved towards the stylet port. The stylet guide means can define at least two non-intersecting stylet paths from parallel axial orientations in the catheter through curved portions to lateral orientations at their stylet ports, the central axes of the paths forming an angle of up to 180° to one other, and wherein a stylet is positioned in each of the stylet paths. The angle between the axes of the paths at the ports can be less than 90°. A preferred angle is 60°.

The medical probe can be used in combination with at least one grounding plate, the grounding plate being adapted to draw electrical current passing from the electrodes through target tissue to be ablated.

The electrode can have a sharp blade tip.

The medical probe can include a control unit attached to the control end of the catheter, a sleeve movement means attached to the non-conductive sleeve and an electrode movement means attached to the electrode enclosed therein. The non-conductive sleeve movement means comprises means for translating manual motion into axial motion of the non-conductive sleeve in the stylet guide means along the longitudinal axis of the sleeve. The electrode movement means comprises means for translating manual motion into axial motion of the electrode in the non-conductive sleeve along the longitudinal axis of the electrode. The non-conductive sleeve movement means and the electrode movement means are movably mounted on the control unit for movement thereon. The non-conductive sleeve movement means and the electrode movement means can include separate, adjacent manual movement means mounted on the control unit for both separate and coordinated movement thereon.

The medical probe can further include means for relating the axial motion of the non-conductive sleeve to inflation of the inflation balloon means. The means for relating the axial motion of the non-conductive sleeve to inflation of the inflation balloon means can comprise a gauge means for measuring the inflation of the balloon means, and graduations on the control unit for accurate manual adjustment of the non-conductive sleeve in relation to the inflation of the balloon means. The means for relating the axial motion of the non-conductive sleeve to inflation of the inflation balloon means can comprise an automatic linkage means for automatically advancing the sleeve in relation to the expansion of the balloon means, the linkage means including a gauge means for measuring the inflation of the balloon means. The automatic linkage means can include a pneumatic or hydraulic cylinder assembly linking the sleeve to the gauge means. The automatic linkage means can instead include a linear electric motor linking the sleeve to the gauge means. The automatic linkage means can instead include an electronic control means for controlling a servo motor.

The control unit can have two parallel longitudinal slots defined in a wall thereof, the movement means each including a finger engageable tab connected to a slide extending through one of the longitudinal slots to a connector in the interior of the housing, in which the one connector is attached to the non-conductive sleeve and the other connector is attached to the electrode.

The method of this invention for medical treatment of a tissue mass comprises the steps of:

a) introducing a catheter along a body duct to a zone adjacent to the target tissue to be treated;

b) moving a flexible stylet comprising a radiofrequency electrode partially enclosed within a non-conductive sleeve, from the catheter through a catheter port in the side wall of the catheter and through surrounding tissue into a target tissue to be treated;

c) exerting an outward force on the wall of the body duct by means of a force exerting means attached to the catheter; and d) generating heat in the target tissue by passing electrode current from the exposed area of the electrode into the target tissue.

The method can comprise moving the non-conductive sleeve means relative to the electrode to expose a preselected area of the electrode in the target tissue to be treated. The position of the non-conductive sleeve can be adjusted in relation to the position of the wall of the body duct. The sleeve position can be automatically adjusted by means of a control means obtaining information from the force exerting means.

The force exerting means can include at least one inflatable balloon, and exerting a force on the wall of the body duct can include inflating the balloon.

The catheter can be positioned adjacent to the target tissue by use of ultrasound imaging.

The catheter can be positioned using a fiber optic scope connected to the catheter.

The stylet can comprise a hollow tube and the temperature of the target tissue being treated can be monitored during the treatment using a temperature sensor mounted in the tube.

Alternatively, the method of this invention can comprise the following steps:

a) advancing a flexible stylet through surrounding tissue into a target tissue to be ablated, the stylet being a radiofrequency electrode surrounded by a moveable non-conductive sleeve means for preventing significant transfer of energy from the electrode to tissue surrounding the sleeve;

b) moving the non-conductive sleeve means to remove it from a preselected portion of the electrode positioned in the target tissue, and generating heat in the target tissue by causing an electric current to flow between the preselected portion of the electrode and a second electrode; and c) exerting a compressive force on the target tissue.

The method can further comprise adjusting the position of the sleeve means as the position of the tissue surrounding the target tissue changes due to the compressive force.

A still further method of this invention comprises the steps of:

a) introducing a catheter up the urethra to a zone adjacent to the prostate target tissue to be treated;

b) moving two flexible stylets, each comprising a radiofrequency electrode partially enclosed within a non-conductive sleeve which is axially moveable relative to the electrode, from the catheter through catheter ports in the side wall of the catheter and through the urethra wall and surrounding tissue into the prostate target tissue to be treated, the catheter ports having axes forming an angle of less than 90° to each other;

c) exerting an outwardly directed force on the urethra wall by means of at least one inflatable balloon attached to the catheter; and d) generating heat in the target tissue by passing electrode current from the exposed areas of the electrodes into the target tissue.

The method can further comprise adjusting the position of the sleeve in relation to changes in position of the urethra wall due to the force exerted on the wall by the inflatable balloon. The angle between the catheter port axes can be 60°. The non-conductive sleeves can be moveable relative to the electrodes and the method can include retracting the sleeves to remove them from preselected portions of the electrodes positioned in the prostate target tissue.

Grounding plates can be placed against the body of the patient to draw electrical current passing from the electrodes through the target tissue to be ablated.

BRIEF DESCRIPTION OF THE DRAWINGS

FIG. 1 is a schematic cross-sectional drawing of the lower male anatomy with one embodiment of the catheter of this invention in position for treatment;

FIG. 2 is a schematic isometric view of the assembly of control console, manual catheter control unit and catheter according to this invention;

FIG. 3 is an isometric view of the control console;

FIG. 4 is a plan view of a control unit and a catheter without balloons;

FIG. 5 is a partial cross-sectional plan view of the probe end of the catheter of FIG. 4;

FIG. 6 is a sectional plan view of one embodiment of the probe end of the catheter of the invention;

FIG. 7 is a sectional plan view of another embodiment of the probe end of the catheter of the invention;

FIG. 8 is a side view of the probe end along line 8—8 of FIG. 7;

FIG. 9 is a sectional plan view of another embodiment of the probe end of the catheter of the invention;

FIG. 10 is a sectional end view of the probe end of FIG. 9;

FIG. 11 is a sectional side view of an electrode used in the catheter;

FIG. 12 is a section through the electrode of FIG. 11 along the line 12—12;

FIG. 13 is a detailed cross-sectional of part of the electrode of FIG. 12 taken along the line 13—13 of FIG. 12;

FIG. 14 is a plan view of a fiber optic scope for use in the catheter of FIG. 7;

FIG. 15 is a detailed cross section of the fiber optic scope of FIG. 14, taken along the line 15—15;

FIG. 16 is a detailed sectional side view of a lens cell attached to the leading end of the scope of FIG. 14;

FIG. 17 is an isometric view of an RF ablation catheter, a catheter control unit and a monitor;

FIG. 18 is an isometric exploded view of another embodiment of a catheter and catheter control unit;

FIG. 19 is an exploded isometric view of part of the catheter control unit of FIG. 18;

FIG. 20 is a partially assembled isometric view of the lower half of the catheter control unit of FIG. 18; and FIG. 21 is an exploded, partially cut-away three-dimensional view of the catheter and an attachment means for the catheter of FIG. 18.

DETAILED DESCRIPTION OF THE INVENTION

The device of this invention provides a precise, controlled positioning of a treatment stylet in a tissue targeted for treatment, destruction or sampling from a catheter positioned in the vicinity of the target tissue. This is described in application Ser. Nos. 07/929,638, now abandoned and 08/012,370, now U.S. Pat. No. 5,370,675, the entire contents of which are incorporated herein by reference.

The term "stylet" as used hereinafter is defined to include both solid and hollow probes which are adapted to be passed from a catheter port through normal tissue to a target tissue. The stylet is shaped to facilitate easy passage through tissue. It can be a solid wire, thin rod, or other solid shape or it can be a thin hollow tube or other shape having a longitudinal lumen for housing a thermocouple or for introducing fluids to or removing materials from a site. The stylet preferably has a sharpened end to reduce resistance and trauma when it is pushed through tissue to a target site.

The stylet can be designed to provide a variety of medically desired treatments of a selected tissue. As a radiofrequency electrode or microwave antenna, it can be used to ablate or destroy the target tissue. As a hollow tube, it can be used to deliver a treatment fluid such as a liquid to a target tissue. The liquid can be a simple solution or a suspension of solids, for example, colloidal particles, in a liquid. Since the stylet is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues is intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with the latter method is iatrogenic sterility. More recently, laser treatment has been employed to remove tissue, limiting bleeding and loss of body fluids.

Microwave therapy has been provided with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue destruction with electrodes positioned within the urethra has limited applicability since it necessarily exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostrate and positions RF electrode stylets directly into the tissues or nodules to be destroyed. The portion of the stylet conductor extending from the urethra to the target tissue is enclosed within a longitudinally adjustable sleeve shield which prevents exposure of the tissue adjacent to the sleeve to the RF current. Thus the ablative destruction is confined to the tissues targeted for destruction, namely those causing the constriction. The catheter includes one or more inflatable annular balloons for exerting an outward force on surrounding tissue. This allows the body canal, for example the urethra, along which the catheter is introduced to be widened. In this way immediate short-term relief may be provided to constricted passageways. In contrast the ablation of tissue surrounding the canal or passageway provides for long-term relief, the effect of which typically takes effect only once the destroyed tissue cells have been removed by the natural body processes. Other aspects of the invention will become apparent from the drawings and accompanying descriptions of the device and method of this invention. It will be readily apparent to a person skilled in the art that this procedure can be used in many areas of the body for percutaneous approaches and approaches through body canals.

FIG. 1 is a schematic cross-sectional drawing of the lower male anatomy showing the use of the device of this invention. The urethra 2 extends from the urinary bladder 4 through the prostate 6 and urogenital diaphragm 8. BPH is a condition characterized by constriction of the portion of the prostatic urethra caused primarily by proliferation of benign glandular and stroma cells in the prostate. These nodules press the wall of the urethra inwardly, restricting the urethral diameter. Traditional treatments short of removal of the prostate have included either removal of tissue from the urethra to enlarge its lumen by resection or laser tissue destruction, or by expansion and heating of the tissue surrounding the urethra to a temperature which causes cell death. The latter method is intended to reduce the swelling or enlargement of the prostate, and restore the urinary passage to at least a portion of its former diameter.

In the method of this invention, a catheter 14 with a pair of stylet guides (not shown) is passed upwardly through the urethra 2 into the prostate 6. The position of the catheter 14 is precisely controlled, using an ultrasound image, for example, obtained from signals received from a conventional ultrasound transducer 18 inserted into the rectum 20 adjacent to the prostate through the anal opening 22. The guides facilitate easy positioning of stylets 24 (one of which is shown in FIG. 1) into a precise location under ultrasound imaging. In addition, fiber optics are used to position the catheter 14. Each stylet includes a non-conductive sleeve 26 surrounding an electrode 28.

The terminal portion of the catheter 14 includes one or more dilation balloons 30 and 32.

The stylet sleeve 26 is extended through the urethra and other tissue to be protected. The RF electrode 28 is then extended deeper into the target tissue 34 or the sleeve 26 is partly retracted once the stylet is in place, leaving the portion of the electrode 28 in the target tissue 34, exposed. Current is then passed through the target tissue 34 from the electrode 28 to a grounding plate 36 in the form of a patch which is affixed to the body; typically to the lower back.

FIG. 2 is a schematic three-dimensional view of the assembly of the control console 50, a manual catheter control unit 52, catheter 54, and power foot control 56. The power foot control 56 functions can be accomplished by numerous other methods including manual digital switches on the control console 50 and a trigger device on the control unit 52. The manual operation of the catheter 54 is controlled from the control unit 52 discussed in greater detail below, with the power control and temperature displays being provided on the control console 50 shown in greater detail in FIG. 3.

FIG. 3 is an isometric representation of an embodiment of the control console 50 of the system of this invention. The housing of this console has a display panel 74 with digital readout displays 76 showing power to the stylet, stylet temperatures, tissue temperatures, impedance values, and other data, for example. The housing can support a sealed membrane switch panel 78 having system control buttons 79. A power cord 80 leads to a standard power outlet. A cable 82 leads to the manual catheter control unit 52 shown in FIG. 2. A Cable 84 leads to an optional power foot control unit. A cable 86 leads to the grounding patch for use in monopolar systems.

FIG. 4 is a top view of one embodiment of a control unit 88 and catheter 90. The unit 88 includes a handle portion 92. The catheter 90 has a distal catheter probe end 93. The distal end 94 of the handle portion 92 is attached to the proximal end of the catheter shaft 95. Manual control tabs 96 and 98 are mounted on the handle portion 92 for sliding engagement with side walls of the handle portion 92. Using the handle 92 for control, the catheter 90 is introduced into a body duct, vascular structure or canal such as the urethra, for example, and pushed up the duct to the treatment position, for example to a position adjacent the prostate. Stylets 100 are individually and selectively passed outward from the distal end 93 through surrounding tissue to the target tissue to be treated by movement of the manual control tab pairs 96 and 98. The stylets are in the form of electrodes 102 surrounded by moveable sleeves 104. The sleeves 104 can be retracted from the end of the stylets by movement of manual control tabs 98 as described in greater detail hereinafter. The unit 88 includes four pairs of control tabs 96, 98 (only four of the tabs are shown) and four stylets 100 (two are shown). The catheter shaft 95 is preferably stiff to facilitate control during penetration along a body duct. The rigidity of the catheter allows it to exert lateral forces on body tissue thereby allowing it to be manipulated along curves in the passageway along which it is passed.

FIG. 5 is a partially sectioned plan view of a two-stylet embodiment of a distal probe end of a catheter with the stylets 106 extended from the side ports 108. The distal probe end comprises a stylet guide housing 110 having lateral surfaces 112 which merge with a tapered tip portion 113. A hollow space or bubble 114 is located on the tapered tip portion 113. The space or bubble 114 reflects ultrasound permitting its easy identification with ultrasound generated by a rectal ultrasound transducer as shown in FIG. 1. The stylets 106 extend outwardly from the lateral surfaces 112 and each comprises an electrode 115 and moveable surrounding sleeve 116. The proximal portion 118 of the stylet guide housing 110 is connected to the distal end 120 of the catheter stem 122. The embodiment shown in FIG. 5 comprises a pair of stylets 106, the stylets 106 extending from ports 108 in a common plane perpendicular to the catheter longitudinal axis. It will be readily apparent to a person skilled in the art that other stylet arrays such as a longitudinal array or a spiral array can also be used, and these variations are considered to be fully within the scope of this invention.

The catheter stem 122 includes an outer tubular housing 124 which encloses a pair of stylet stems 126 disposed in a parallel relationship. The individual stylets are directed outward in paths 128 which serve as stylet guide means and which have axes at the side ports forming angles of 180° to each other in a plane perpendicular to the longitudinal axis of the stylet guide housing 110. It will be appreciated that the side ports 108 could be located less than 90° to one another, for example 60° apart so that the stylets extend outwardly at 60° to one another in a plane perpendicular to the longitudinal axis of the housing 110.

Another embodiment of the distal probe end of the catheter is illustrated in FIG. 6 and is indicated by reference numeral 130. The distal probe end 130 includes a stylet guide housing 132 which is similar in structure to the housing described with reference to the embodiment illustrated in FIG. 5. The housing 132 has a round cylindrical outer surface and terminates in a distal rounded end 134. The housing 132 is made of a rigid polycarbonate material and defines two guide paths 136 for guiding ablation stylets (not shown) as for the embodiment illustrated in FIG. 5. The distal probe end 130 further includes two annular dilation balloons 140 spaced axially along the outer surface 142 of the housing 132. Side ports 144 through which the stylets are extendable into surrounding tissue are located between the two annular balloons 140. The housing 132 further defines a longitudinally extending fluid supply lumen 150. The lumen 150 supplies saline solution or other liquid or gas to the balloons 140 by means of radially extending connecting passageways 152. Saline solution supplied from the control unit (not shown) inflates the balloons 140, causing them to extend radially from the outer surface 142 of the housing 132. The balloons are made of any suitable elastic material, for example silicon rubber or latex rubber, and are adhesively attached to the outer wall 142 of the housing 132 by means of an adhesive, for example polyurethane or epoxy glue.

As illustrated in FIG. 6, the axes of the paths 136 at the ports 144 are perpendicular to the outer surface 142. This is necessary where it is envisaged that the inflation of the balloons 140 take place while the stylets are extended. Lateral outward movement of surrounding tissue would exert lateral forces on the stylets if they were to extend in planes which are not perpendicular to the outer surface 142 of the housing 132. It will be appreciated that this is not a requirement where the inflation of the balloons 140 takes place while the stylets are in a retracted state.

As in the embodiment illustrated in FIG. 5, each stylet 154 includes an electrode 156 slidably housed within an outer sleeve 158. The non-conductive sleeve 158 has a leading tapered tip 159, a rigid proximal control section (not shown) and a flexible intermediate portion 160 extending from the leading tip 159 to the rigid proximal control section, enabling the sleeve 158 to be extended from an axial orientation to an orientation in which the sleeve 158 extends outwardly through the stylet port 144. The sleeve 158 is made of an electrically non-conductive material or can be made of a spiral coil or wire braid which is covered with a non-conductive material. The sleeve 158 is adjustable to expose only a portion of the electrode 156. This ensures that only a predetermined portion of the tissue is heated. In the case where the catheter is passed along the male urethra to perform ablative treatment on the prostate gland, it is essential that the urethra wall be protected against destructive heating by the electrode 156. To ensure this the position of the sleeve 158 has to be adjusted to accommodate changes in the position of the urethra wall 161 as the balloons 140 are inflated. This may be achieved by having calibrations on the control unit (not shown) as is described below for adjusting the extension of the sleeves 158. By monitoring the amount of saline solution fed to the balloons 140 and knowing their corresponding radial extension, the sleeves 158 can be accurately adjusted to accommodate changes in the position of the urethra wall 161.

Instead a mechanical linkage or microprocessor controlled control system can be provided for automatically adjusting the extension of the sleeve 158 in accordance with the inflation of the balloons 140. In such an embodiment the volume of saline solution supplied by a supply source is monitored by means of a suitable gauge. Signals from the gauge are used to control a mechanical drive mechanism, for example a servomotor attached to the sleeve 158. Instead of monitoring the volume of saline, the pressure in the balloons 140 can be monitored. In yet another method the position of the balloon outer wall or the urethra wall can be monitored, for example visually using an ultrasound or fiber optic scope. In each case the parameter measured is used to control the position of the sleeve 158.

Another embodiment of the distal probe end is illustrated in FIG. 7 and is indicated by reference numeral 170. Again the probe end 170 comprises a circular cylindrical housing 172 having a rounded front end 174. As in the embodiment of FIG. 6, the housing 172 defines a pair of stylet guide means in the form of stylet paths 176 exiting the housing at ports 178. The pathways 176 guide the stylets 179 along respective curved paths to exit the housing 172 in a plane perpendicular to the longitudinal axis of the housing 172. As is shown, each path 176 has a first curved portion 180 curved away from the stylet port 178, and a second curved portion 181 curved towards the stylet port 178. The second curved portion typically has a radius of at least 0.5 cm. However the radii of the second curved portions may be reduced even further by using appropriate materials for the stylets 179 or by reducing the thickness of the stylets sufficiently. The distal probe end 170 differs from that illustrated in FIG. 6 insofar as only one dilation balloon 182 is provided. The balloon 182 takes the form of a bladder having an outer wall 184 and an inner wall 186. As is more clearly illustrated in FIG. 8, the balloon defines a pair of openings 188 to allow free passage of the stylets 179 through the openings 188. Typically the distal probe end will be designed so that the stylets extend at an angle between 0° and 90° to each other. In a preferred embodiment the two ports 178 with their aligned openings 188 are circumferentially spaced from each other so as to direct the stylets radially outwardly at an angle of 60° relative to one another.

A fluid supply lumen 190 extends into an opening in the inner wall 186, the inner wall being firmly secured, for example by means of an adhesive, to the outer surface 192 of the housing 172.

The housing 172 further defines a longitudinally extending fiber optic channel 194 for supporting a fiber optic scope which will be described in greater detail below. The channel 194 extends all the way to the rounded front end 174 of the housing 172 to define a viewing port 196 to provide visual information. Typically the viewing port provides a viewing angle of between 70° and 90°.

Temperature sensors 197, 198 are mounted on the balloon 182 and sleeve 199, respectively. The sensor 197 monitors the temperature of the tissue abutting the balloon 182. The sensor 198, in turn, monitors the temperature of the target tissue.

As with the embodiment illustrated in FIG. 6, the embodiment of FIG. 7 requires adjustment of the sleeves 199 when the balloon 182 is inflated or deflated. One way of overcoming this problem is by adopting the embodiment illustrated in FIGS. 9 and 10. FIG. 9 shows a sectional plan view of another embodiment of the probe end of the catheter of the invention and FIG. 10 shows a sectional end view through the probe end. The probe end of the catheter in this embodiment is indicated by reference numeral 200 and includes a stylet guide housing 202 which is similar to the structure of the housing described with reference to the embodiment illustrated in FIG. 6. In this embodiment the probe end 200 is provided with a single annular dilation balloon 203 which is bonded to the housing 202 in a manner similar to that described for the embodiment of FIG. 6. This embodiment differs from that in FIG. 6 insofar as the stylets 204 (shown only in FIG. 10) pass through the balloon 203. For this purpose the balloon is bonded to that part of the outer surface of the housing 202 which defines the stylet ports 205, as illustrated in FIG. 10. The ports 205 for the stylets 204 are aligned with holes in the balloon at the portion bonded to the housing 202. The balloon 203 is illustrated in its collapsed state in FIG. 10. A possible expanded position of the balloon is illustrated by the broken line in FIG. 10. It will be appreciated that as the balloon 203 expands the side of the housing 202 from which the stylets 204 extend, will be urged into abutment with the urethral wall. Consequently, dilation of the urethra will not cause any movement of that part of the urethral wall which is in abutment with the insulating sleeves 206 of the stylets 204, relative to the sleeves 206. There is therefore no need for any adjustment in the position of the sleeves 206 as the balloon 203 is inflated or deflated.

FIG. 11 shows a sectional side view of one embodiment of an electrode 208. The electrode 208 comprises a nickel-titanium tube 210. The tip 211 of the electrode 208 is formed by sealing the front end of the tube 210 by means of a titanium inert gas weld (shown in broken lines) which is then ground down to form a sharpened tip 211. A thermocouple 212 is mounted within the tube 210, at the tip of the electrode 208 by means of a thermally conductive potting compound, for example a silver or aluminum filled epoxy 213. A further thermocouple 214 is slidably mounted within the tube 210 in a manner more clearly illustrated in FIGS. 12 and 13. FIG. 12 is a cross-sectional view along the line 12—12 of FIG. 11. The tube 210 is partially filled with a potting compound 215. Referring to FIG. 13, the thermocouple 214 is secured to a spring 216 by conventional means, for example, by means of an adhesive. The spring 216 is mounted on a metallic slide member 218, for example, by means of an adhesive 219. The slide member 218 extends along the electrode 208 and is slidable relative to the potting compound 215 thereby allowing the thermocouple 214 to be moved along the electrode 208. The spring 216 abuts the inner wall of the tube 210 thus placing the thermocouple in physical contact with the tube 210 for better heat transfer. This ensures good thermal contact between the thermocouple 214 and the electrode 208. The thermocouple 214 is typically encased in an electrically non-conductive coating and the thermocouple leads 220, 222 extend along the cavity 224 defined by the electrode 208.

FIG. 14 shows a fiber optic scope 230 for use with a catheter having a fiber optic channel as shown in the FIG. 7 embodiment. Referring to FIG. 15, the scope 230 comprises a plurality of viewing fibers 232 surrounded by light fibers 234. The light fibers 234 illuminate the tissue target area and the viewing fibers 232 relay an optical image of the target area. A stainless steel sheath 236 surrounds the fibers 234. The fiber optic scope 230 typically has a diameter of approximately 0.07 inches. Referring to FIG. 14, the scope 230 is connected at its proximal end to a tri-coupler 238. The tri-coupler 238 has a viewing output 240, a light input 242 and a fluid input 244. Fluid injected into the input 244 exits the tri-coupler at a port 246 and is channeled along the outer surface of the sheath 236 by means of the fiber optic channel 194 (FIG. 7).

In order to provide an appropriate viewing field of 70° to 90° at the front end of the catheter, the fiber optic scope 230 includes a lens cell attached to the distal end of the fibers 232, 234. A sectional side view of the lens cell 250 is illustrated in FIG. 16. It comprises two opposed lenses 252, 254 having inwardly facing, opposed convex surfaces which are coaxially aligned by means of a stainless steel sleeve 256. Each lens 252, 254 is made by grinding a spherical crystal to define a flat face 258. The crystal is also ground circumferentially to define a circumferentially extending surface 260 perpendicular to the face 258. The diameter of the resultant cylindrical portion of each crystal is dimensioned such that it is receivable in the sleeve 256.

FIG. 17 is a three-dimensional view of a two stylet embodiment of an RF ablation catheter not having inflation balloons but which makes use of a fiber optic scope. The rigid catheter 300 is attached to a control unit 302. The catheter 300 has a terminal stylet guide housing 304 with two stylets 306 and 308 extendable in a plane perpendicular to the longitudinal axis of the catheter 300. The control unit 302 has stylet sleeve control tabs 310 and electrode control tabs 312 as will be described in greater detail hereinafter. A tri-coupler 313 is attached to the control unit 302. The tri-coupler 313 is connected to a fiber optic scope as was described with reference to FIG. 14, or to a solid rod lens. The proximal end of the tri-coupler 313 is connected to a video camera 314. The camera 314 is, in turn, connected to a visual monitor 315. A RF power connector 316 and a thermocouple connector 318 are also connected electrically to the control unit 302. The portion of the catheter 300 leading from the control unit 302 to the stylet guide housing 304 is rigid and can, for example, be made of a polycarbonate material.

Another embodiment of the catheter and control unit, which includes the feature of a fiber optic scope, is illustrated in FIGS. 18 to 21. FIG. 18 shows a three-dimensional exploded view of the control unit from below. The catheter 330 is connected to the control unit 332 by means of a connector 334 which will be described in greater detail below with reference to FIG. 21. The control unit 332 includes a housing 336. The housing 336 has a lower half 338 and an upper half 340 which have complimentary flange formations 342 and 344, respectively, along opposed edges for complimentary engagement of the two halves. The housing 336 is angled downwardly towards its proximal end 350 and the lower half 338 is provided with a ribbed outer surface 352. This allows easier handling by an operator.

The upper half 340 defines an opening 354 in its upper wall 356. The opening 354 is dimensioned to be engageable by a fiber optic scope port 358 which includes a cylindrical guide portion 360. The guide portion 360 is sealable by means of a plug 362 when not in use and is held in place by means of a bracket 364 having engagement formations 366 engageable with complimentary sockets 368 on the upper half 340.

Referring to FIG. 19, the upper half 340 further includes a pair of outer longitudinally extending outer slots 370 and a pair of longitudinally extending inner slots 372. The outer slots 370 receive slide formations 374 of stylet sleeve control tabs 376. In a similar fashion, the inner slots 372 receive slide formations 378 of electrode control tabs 380. Each stylet sleeve control tab 376 is slidably secured in a slot 370 by means of a key 384. The slide formation 374 engages a complimentary aperture 382 in the key 384 and is retained there by means of a suitable clip (not shown). In a similar fashion the slide formation 378 engages an aperture 386 in a key 388. The keys 384 and 388 slidably engage one another. The key 382 has a front lip 389 which acts as an abutment formation for a tab 390 on the key 384. In order to provide the slide formations 374, 378 with a certain frictional resistance to their sliding movement, friction pads 391 connected by a spring 392 are mounted on a friction pad support housing 393. The friction pad support housing 393 is mounted between the key 388 and the inner surface of the upper half 340. The tab 390 further includes a vertically extending hole 394 which receives a machine screw 396 illustrated in FIG. 18. The key 388 is provided with a bore 398 for receiving a second machine screw 400 (FIG. 18).

Referring to FIG. 18, the screws 396 and 400 pass through holes in tabs 402 and 404, respectively. The tab 402 is secured to an external hypotube 406 while the tab 404 is secured to an inner hypotube 408 which is slidably received in the tube 406. The outer hypotube 406 is secured to a stylet sleeve (not shown). The tube 408 is in turn attached to an electrode (not shown) which is slidably received in the stylet sleeve.

The two pairs of hypotubes 406, 408 (only one of which is shown in FIG. 18) extend into channels defined by tubes 410, more clearly illustrated in FIG. 21. As is shown in FIG. 21 the two tubes 410 abut a third longitudinally extending tube 412 which defines a fiber optic channel for the fiber optic scope. The catheter 330 is secured to the control unit 332 by means of a pivot connector 414. The pivot connector 414 includes a hub 416 secured to the housing 336 by means of spigots 418, 420 receivable in complimentary sockets 422, 424, respectively as illustrated in FIG. 18. The connector housing 426 is rotatably mounted on the hub 416 by means of a pair of brackets 428. The brackets 428 are engageable with the hub 416 and are secured to the connector housing 426 by being slidably received in the housing 428. Hooks 429 extend from leading ends of the brackets 426 and engage complementary formations (not shown) on the housing 426.

As illustrated in FIG. 20, the housing further includes an electrical connector 430 which is received in complimentary cutout sections in rear walls of the lower and upper halves 338, 340 (FIG. 18). The connector 430 connects internal conductors 432 for the electrodes and thermocouples to external power supplies (not shown).

It will be appreciated that by manipulating the control tabs 376, the sleeves 434 (FIG. 20) attached to the control tabs 376 may be extended along the catheter 330. The sleeves 434 exit the catheter at the distal end 436 via ports 438 (one of which is shown in FIG. 21). Similarly manipulation of the control tabs 380 allows the electrodes 440 (FIG. 20) to be extended through the ports 438 independently of the sleeves 434. The extension of the sleeves 434 over the electrodes 440 is however limited by the tabs 390 engaging the lips 389. In this way the sleeves 434 do not extend substantially beyond the tips of the electrodes 440.

The sleeves can be manually manipulated so as to protect the urethra wall during heating of the target tissue. Simultaneously with or before or after the ablation process inflatable balloons (if provided) can be inflated to exert an outward pressure on the urethra wall. As the urethra wall is forced outwardly the stylet sleeves are adjusted manually or automatically as described above. It will be appreciated that the balloons could be replaced by any suitable force exerting means, for example outwardly extendable ribs.

The invention claimed is:

1. A medical probe device for medical treatment of tissue at a treatment site through a natural body opening defined by a wall, comprising an elongate guide housing having proximal and distal extremities and having a passageway therein extending from the proximal extremity to the distal extremity along a longitudinal axis, a stylet mounted in the guide housing and having proximal and distal extremities, a handle mounted on the proximal extremity of the guide housing, means mounted on the proximal extremity of the guide housing and connected to the stylet for causing advancement of the stylet through the passageway, the distal extremity of the guide housing being in communication with the passageway and permitting the distal extremity of the stylet to be advanced out of the passageway sidewise at an angle with respect to the longitudinal axis into the tissue, the stylet including a conductive radio frequency electrode and a layer of insulating material coaxially disposed on the conductive radio frequency electrode so that a predetermined portion of the conductive radio frequency electrode is exposed in the tissue and the layer of insulating material protects the wall and expandable balloon means mounted on the guide housing for engaging the wall.

2. A medical probe of claim 1 wherein the balloon means includes at least one dilation balloon and wherein the guide housing is provided with a fluid delivery lumen extending from the proximal extremity to the distal extremity of the guide housing so as to be in communication with the dilation balloon whereby the dilation balloon expands outwardly from the distal extremity of the guide housing when fluid is supplied from the fluid delivery lumen to the dilation balloon.

3. A medical probe of claim 1 wherein the guide housing is provided with a lumen extending in a direction parallel to the longitudinal axis, the lumen having a proximal opening for receiving a scope and a distal viewing port.

4. A medical probe of claim 3 wherein the scope includes viewing fibers, light fibers and a liquid supply connector for supplying a flushing liquid to the distal extremity of the guide housing.

5. A medical probe of claim 1 wherein the stylet comprises a tube having an axial lumen extending longitudinally therethrough.

6. A medical probe of claim 5 wherein the tube is made of nickel-titanium.

7. A medical probe of claim 5 wherein a temperature sensor is slidably disposed in the axial lumen.

8. A medical probe of claim 1 including a temperature sensor mounted on the balloon means for measuring the temperature adjacent the balloon means.

9. A medical probe of claim 1 including a temperature sensor carried by the layer of insulating material.

10. A medical probe of claim 1 together with an additional stylet mounted in the guide housing.

11. A medical probe of claim 10 wherein the guide housing includes two stylet ports positioned approximately in a plane perpendicular to the longitudinal axis.

12. A medical probe of claim 1 together with ultrasound imaging means carried by the distal extremity of the guide housing.

13. A medical probe of claim 1 together with a stylet guide means carried by the distal extremity of the guide housing for directing the stylet sidewise at an angle with respect to the longitudinal axis, the stylet guide means defining a stylet path from an axial orientation in the guide housing through a curved portion to a lateral orientation.

14. A medical probe of claim 13 wherein the curved portion has a radius which is sufficient to permit sliding deployment of the stylet in the stylet path.

15. A medical probe of claim 14 wherein the stylet guide means defines a stylet path terminating at a stylet port, the stylet path having a first curved portion which curves away from the stylet port and a second curved portion continuing from the first curved portion which curves towards the stylet port.

16. A medical probe of claim 13 wherein the stylet guide means defines at least two non-intersecting stylet paths from parallel axial orientations in the guide housing through curved portions to lateral orientations at respective stylet ports, the central axes of the stylet paths at the stylet ports forming an angle of up to 180° to one other and wherein a stylet is slidably disposed in each of the stylet paths.

17. A medical probe of claim 16 wherein the angle between the axes of the stylet paths at the stylet ports is less than 90°.

18. A medical probe of claim 16 wherein the angle between the axes of the stylet paths at the stylet ports is 60°.

19. A medical probe of claim 13 wherein the stylet guide means is made from a polycarbonate.

20. A medical probe of claim 1 in combination with at least one grounding plate, the grounding plate adapted to draw electrical energy passing from the conductive radio frequency electrode through target tissue to be ablated.

21. A medical probe of claim 1 wherein the stylet has a sharpened tip.

22. A medical probe of claim 1 wherein the layer of insulating material is an insulating sleeve coaxially mounted on the conductive radio frequency electrode.

23. A medical probe device of claim 22 wherein the insulating sleeve is mounted for longitudinal movement on the conductive radio frequency electrode.

24. A medical probe of claim 22 wherein the means for causing advancement of the stylet through the passageway includes means connected to the conductive radio frequency electrode and the insulating sleeve for causing relative movement between the insulating sleeve and the conductive radio frequency electrode so that a preselected length of the conductive radio frequency electrode can be exposed.

25. A medical probe of claim 24 wherein the means for causing relative movement between the insulating sleeve and the conductive radio frequency electrode include separate, adjacent manual movement means mounted on the handle for both separate and coordinated movement thereon.

26. A medical probe of claim 25 together with means for relating movement of the insulating sleeve to inflation of the balloon means which includes gauge means for measuring the inflation of the balloon means and graduations on the handle for accurate manual adjustment of the insulating sleeve in relation to the inflation of the balloon means.

27. A medical probe of claim 24 together with means for relating movement of the insulating sleeve to inflation of the balloon means.

28. A medical probe of claim 27 wherein the means for relating movement of the insulating sleeve to inflation of the balloon means includes automatic linkage means for automatically advancing the sleeve in relation to the expansion of the balloon means, the linkage means having gauge means for measuring the inflation of the balloon means.

29. A medical probe of claim 28 wherein the linkage means includes a pneumatic or hydraulic cylinder assembly linking the sleeve to the gauge means.

30. A medical probe of claim 28 wherein the linkage means includes a linear electric motor linking the sleeve to the gauge means.

31. A medical probe of claim 28 wherein the linkage means includes a servo motor linking the sleeve to the gauge means and electronic control means for controlling the servo motor.

32. A method for medical treatment of a tissue mass comprising:
    (a) introducing a catheter along a body duct to a zone adjacent to the target tissue to be treated;
    (b) moving a flexible stylet comprising a radiofrequency electrode partially surrounded by a non-conductive sleeve from the catheter through a catheter port and surrounding tissue into a target tissue to be treated;
    (c) exerting an outward force on the wall of the body duct by means of a force exerting means attached to the catheter; and
    (d) generating heat in the target tissue by passing electrical energy from an exposed area of the electrode into the target tissue.

33. A method of claim 32 comprising moving the non-conductive sleeve relative to the electrode to expose a preselected area of the electrode in the target tissue to be treated.

34. A method of claim 33 wherein the position of the non-conductive sleeve is adjusted in relation to the position of the wall of the body duct.

35. A method of claim 34 wherein the sleeve position is automatically adjusted by means of a control means obtaining information from the force exerting means.

36. A method of claim 32 wherein the force exerting means includes at least one inflatable balloon and wherein exerting a force on the wall of the body duct includes inflating the balloon.

37. A method of claim 32 wherein the catheter is positioned adjacent to the target tissue by use of ultrasound imaging.

38. A method of claim 32 wherein the catheter is positioned using a scope connected to the catheter.

39. A method of claim 32 wherein the stylet comprises a hollow tube and wherein the temperature of the target tissue being treated is monitored during the treatment using a temperature sensor disposed in the tube.

40. A method for treatment of target tissue without exposing tissue surrounding the target tissue to destructive temperatures comprising:
    (a) advancing a flexible stylet through surrounding tissue into the target tissue to be ablated, the stylet being a radiofrequency electrode surrounded by a moveable non-conductive sleeve means for preventing significant transfer of energy from the electrode to tissue surrounding the sleeve;
    (b) moving the non-conductive sleeve means to expose a preselected portion of the electrode positioned in the target tissue and generating heat in the target tissue by causing electrical energy to flow between the preselected portion of the electrode and a second electrode; and
    (c) exerting a compressive force on the target tissue.

41. A method of claims 40 further comprising adjusting the position of the sleeve means as the position of the tissue surrounding the target tissue changes due to the compressive force.

42. A method for treating a target tissue such as the prostate of a patient comprising:
    (a) introducing a catheter into the urethra to a zone adjacent to the prostate target tissue to be treated;
    (b) moving two flexible stylets, each comprising a radiofrequency electrode partially surrounded by a non-conductive sleeve which is axially moveable relative to the electrode, from the catheter through catheter ports and through the urethra wall and surrounding tissue into the prostate target tissue to be treated, the catheter ports having respective axes disposed relative to each other at an angle of less than 90°;
    (c) exerting an outwardly directed force on the urethra wall by means of at least one inflatable balloon attached to the catheter; and
    (d) generating heat in the target tissue by passing electrical energy from the exposed areas of the electrodes into the target tissue.

43. A method of claim 42 further comprising adjusting the position of the sleeve in relation to changes in position of the urethra wall due to the force exerted on the wall by the inflatable balloon.

44. A method of claim 42 wherein the axes are disposed relative to each other at an angle of 60°.

45. A method of claim 42 wherein the method includes retracting the sleeves relative to the electrodes to expose preselected portions of the electrodes positioned in the prostate target tissue.

46. A method of claim 42 wherein grounding plates are placed against the body of the patient to draw electrical energy passing from the electrodes through the target tissue to be ablated.

47. A medical probe device for medical treatment of tissue of a prostate through a urethra defined by a urethral wall comprising a guide housing having proximal and distal extremities and having a passageway extending from the proximal extremity to the distal extremity, a stylet slidably mounted in the passageway of the guide housing, guide means carried by the distal extremity of the guide housing and in communication with the passageway for directing the stylet sidewise of the guide housing, the stylet including a flexible radio frequency electrode with a sharpened tip and an insulating sleeve slidably disposed on the radio frequency electrode, handle means mounted on the proximal extremity of the guide housing for introducing the distal extremity of the guide housing into the urethra to the vicinity of the prostate, the handle means including means secured to the stylet for advancing the stylet from the passageway of the guide housing to cause the sharpened tip of the radio frequency electrode and the insulating sleeve to penetrate the urethral wall and to extend into the tissue of the prostate with the insulating sleeve extending through the urethral wall, the handle means also including means for causing relative movement between the insulating sleeve and the radio frequency electrode to expose a predetermined length of the radio frequency electrode in the tissue of the prostate with the insulating sleeve extending through the urethral wall, means for supplying radio frequency energy to the radio frequency electrode to cause the temperature of the tissue of the prostate adjacent the predetermined length of the radio frequency electrode to be raised to cause destruction of cells in the tissue of the prostate, the guide housing having a fluid delivery lumen extending from the proximal extremity to the distal extremity of the guide housing and inflatable balloon means mounted on the distal extremity of the guide housing in communication with the fluid delivery lumen.

48. A medical probe as in claim 47 wherein the balloon means extends around only a portion of the distal extremity of the guide housing.

49. A medical probe as in claim 48 wherein the balloon means is expandable from said portion of the distal extremity of the guide housing and the stylet extends sidewise of the guide housing from another portion of the distal extremity of the guide housing which is generally opposite to said first-named portion.

50. A medical probe as in claim 47 wherein the stylet passes through the balloon means as it extends sidewise of the guide housing.

51. A medical probe as in claim 47 together with an additional stylet slidably mounted in the passageway of the guide housing which is of the same type as said first-named stylet.

52. A medical probe as in claim 47 wherein the balloon means includes an annular balloon.

53. A method for the treatment of benign prostatic hypertrophy in the prostate of the human male having a bladder with a base and a penis with a urethra therein formed by a urethral wall extending into the base of the bladder along a longitudinal axis with the prostate having tissue surrounding the urethra near the base of the bladder, comprising dilating the urethra in the vicinity of the prostate with an expandable balloon disposed in the urethra, selecting a target volume of the tissue of the prostate beyond the urethral wall, introducing radio frequency energy through the urethral wall into the target volume of the tissue of the prostate to cause ablation of tissue in the target volume of the tissue in the prostate and protecting the urethral wall from ablation by the radio frequency energy supplied to the target volume of tissue in the prostate.

54. A method as in claim 53 together with a radio frequency electrode formed of an electrically conductive material and a layer of insulating material surrounding at least a portion of the radio frequency electrode, further comprising the step of introducing the radio frequency electrode into the target volume of the tissue of the prostate with the layer of insulating material extending through the urethral wall, the radio frequency energy being supplied to the radio frequency electrode.

55. A method as in claim 54 wherein the layer of insulating material is an insulating sleeve slidably mounted on the radio frequency electrode, further comprising the step of causing relative sliding movement between the radio frequency electrode and the insulating sleeve to expose a preselected length of the radio frequency electrode corresponding to the size of the target volume while retaining the insulating sleeve in a position so that it continues to extend through the wall.

56. A method for medical treatment of a prostate through a urethra formed by a urethral wall by the use of a catheter having a distal extremity carrying expandable balloon means and having a flexible radio frequency electrode with a sharpened tip and an insulating sleeve mounted on and surrounding the flexible radio frequency electrode to expose a predetermined length of the radio frequency electrode, the radio frequency electrode and the insulating sleeve being slidably mounted in the catheter and being movable through the distal extremity of the catheter, comprising introducing the catheter through the urethra to a region adjacent the prostate, expanding the balloon means in the urethra, advancing the flexible radio frequency electrode and the insulating sleeve using the sharpened tip to penetrate the urethral wall and pass through the urethral wall into the prostate, passing sufficient radio frequency energy through the radio frequency electrode to raise the temperature of the prostate adjacent the predetermined length of the radio frequency electrode to a temperature causing destruction of cells by ablation in the prostate while protecting the urethral wall by the insulating sleeve from the radio frequency energy.

57. A method as in claim 56 wherein the radio frequency electrode and the insulating sleeve are movable relative to each other, further comprising the step of establishing a relationship between the radio frequency electrode and the insulating sleeve so that a predetermined portion of the radio frequency electrode extends out of the insulating sleeve and is exposed in the prostate.

58. A method as in claim 56 further comprising the step of expanding the balloon means along one side of the distal extremity of the catheter so as to urge the catheter against the urethral wall.

59. A method as in claim 56 wherein the advancing step includes advancing the radio frequency electrode and the insulating sleeve through the balloon means.

* * * * *